United States Patent
Shuman et al.

(10) Patent No.: US 10,441,254 B2
(45) Date of Patent: Oct. 15, 2019

(54) BIOPSY SAMPLE RETENTION MECHANISM

(71) Applicant: SPIRATION, INC., Redmond, WA (US)

(72) Inventors: Brandon J. Shuman, Kirkland, WA (US); David H. Dillard, Grapeview, WA (US)

(73) Assignee: SPIRATION, INC, Redmond, WA (US)

( * ) Notice: Subject to any disclaimer, the term of this patent is extended or adjusted under 35 U.S.C. 154(b) by 119 days.

(21) Appl. No.: 15/552,570

(22) PCT Filed: Mar. 22, 2016

(86) PCT No.: PCT/US2016/023516
§ 371 (c)(1),
(2) Date: Aug. 22, 2017

(87) PCT Pub. No.: WO2016/154170
PCT Pub. Date: Sep. 29, 2016

(65) Prior Publication Data
US 2018/0049730 A1     Feb. 22, 2018

Related U.S. Application Data

(60) Provisional application No. 62/138,728, filed on Mar. 26, 2015.

(51) Int. Cl.
*A61B 10/02*     (2006.01)
*A61B 17/34*     (2006.01)
(Continued)

(52) U.S. Cl.
CPC .............. *A61B 10/04* (2013.01); *A61B 1/018* (2013.01); *A61B 1/2676* (2013.01);
(Continued)

(58) Field of Classification Search
CPC .............. A61B 10/0233–0283; A61B 17/3478
See application file for complete search history.

(56) References Cited

U.S. PATENT DOCUMENTS 3,882,849 A      5/1975  Jamshidi
5,993,408 A  *  11/1999  Zaleski .............. A61F 9/00745
                                                           604/22
(Continued)

FOREIGN PATENT DOCUMENTS

EP      0186256 A1    7/1986
EP      1905361 A1    4/2008
(Continued)

OTHER PUBLICATIONS

Japanese Office Action from Application No. JP 2017-549283 dated Aug. 28, 2018.
(Continued)

*Primary Examiner* — Thaddeus B Cox
(74) *Attorney, Agent, or Firm* — The Dobrusin Law Firm, P.C.; Daniel P. Aleksynas (57) ABSTRACT

An apparatus, comprising: a biopsy needle having a distal end and a proximal end, all or a portion of the biopsy needle being movable between a collapsed state and an expanded state; a sheath having a distal end and a proximal end, wherein the biopsy needle in the collapsed state is contained within the sheath, and in the expanded state at least the distal end of the biopsy needle extends from the distal end of the sheath; wherein the biopsy needle is provided with two or more sleeves, which at least partially overlap in the collapsed configuration and which cylindrically expand to provide an increased radius, relative to a radius in the collapsed state, for sampling in the expanded configuration,
(Continued)

and wherein a cross section of the distal end of the biopsy needle in the expanded state is a substantially circular cross section.

20 Claims, 7 Drawing Sheets

(51) Int. Cl.
*A61B 10/04* (2006.01)
*A61B 1/018* (2006.01)
*A61B 1/267* (2006.01)
*A61B 17/00* (2006.01)

(52) U.S. Cl.
CPC ...... *A61B 10/0266* (2013.01); *A61B 17/3478* (2013.01); *A61B 2010/045* (2013.01); *A61B 2017/0034* (2013.01); *A61B 2017/00867* (2013.01)

(56) References Cited

U.S. PATENT DOCUMENTS

| | | | |
|---|---|---|---|
| 6,036,698 A | 3/2000 | Fawzi et al. | |
| 6,142,957 A | 11/2000 | Diamond et al. | |
| 6,155,989 A | 12/2000 | Collins | |
| 7,608,048 B2 | 10/2009 | Goldenberg | |
| 8,911,467 B2 | 12/2014 | Mitelberg et al. | |
| 2004/0210306 A1 | 10/2004 | Quijano et al. | |
| 2005/0080355 A1 | 4/2005 | Mark | |
| 2007/0106176 A1 | 5/2007 | Mark | |
| 2007/0232992 A1 | 10/2007 | Kutsko et al. | |
| 2008/0249558 A1 | 10/2008 | Cahill | |
| 2008/0300507 A1* | 12/2008 | Figueredo | A61B 10/0266 600/567 |
| 2010/0049307 A1 | 2/2010 | Ren | |
| 2010/0298736 A1 | 11/2010 | Levy | |
| 2013/0046334 A1 | 2/2013 | Jones et al. | |
| 2013/0090624 A1 | 4/2013 | Munsinger | |
| 2016/0015372 A1* | 1/2016 | Walak | A61B 10/0266 600/567 |
| 2016/0249990 A1* | 9/2016 | Glozman | A61B 34/30 606/130 |

FOREIGN PATENT DOCUMENTS

| | | |
|---|---|---|
| JP | 2005/137454 A | 6/2005 |
| JP | 2008/528207 A | 7/2008 |
| WO | 89/10092 A1 | 11/1989 |
| WO | 2012/024227 A1 | 2/2012 |
| WO | 2013/135792 A1 | 9/2013 |
| WO | 2014/049783 A1 | 4/2014 |
| WO | 2014/112518 A1 | 7/2014 |
| WO | 2015/004571 A1 | 1/2015 |

OTHER PUBLICATIONS

International Search Report and Written Opinion for Application No. PCT/US2016/023516 dated Aug. 9, 2016.
Co-pending U.S. Appl. No. 62/138,729, filed Mar. 26, 2015.

* cited by examiner

BIOPSY SAMPLE RETENTION MECHANISM

FIELD

The present teachings generally relate to a biopsy device and specifically to a biopsy device including a needle having one or more mechanisms to assist in retaining a sample within the needle.

BACKGROUND

The present teachings are predicated upon providing a large continuous tissue sample during a biopsy so that an accurate assessment can be made. Current systems include a needle that extends into tissue and vacuum is applied to assist in retaining the sample within the needle. An adequate or reliable sample may not be removed on the first attempt and, thus, the needle may have to be extended into a tissue sample multiple times before a sufficient sample is removed. Repeatedly extending the needle into a location may result in increased trauma to an area, multiple small samples being taken, or both. Additionally, an application of suction during sampling may cause fluids to be drawn into the needle with the sample, may cause small particles of sample to be drawn into the needle, or both. If too much fluid, such as blood, is drawn into the needle during sampling, the sample may be compromised and may not be usable, and if the samples are too small the samples may not be usable.

Current needles used to perform a biopsy are limited in size by the size of the endoscope or bronchoscope used in a procedure or the size of the sheath that extends from one or more of the channels of the endoscope or bronchoscope. As the size of the channels in the endoscope or bronchoscope become smaller the sizes of the needles being used become smaller, which limits the size of the sample that can be taken. Examples of biopsy devices may be found in U.S. Pat. No. 8,911,467; and International Patent Application Publication No. WO2015/004571; all of which are incorporated by reference herein in their entirety for all purposes.

It would be attractive to have a needle that is expandable to take a sample that is larger than the size (e.g., diameter) of the needle while the needle is located within the sheath and/or delivery device. What is needed is a device to assist in retaining the sample within the needle once a sample is taken without the application of vacuum or with a reduced application of suction. It would be attractive to have a device that resists the sample from being pulled from the needle when the needle is retracted. What is needed is a device that assists in cutting an attached portion of a sample or prevents removal of a sample due to an attached portion. It would be attractive to have a device that rotationally cuts a sample while the needle is extended axially into a sample site.

SUMMARY

The present teachings meet one or more (if not all) of the present needs by providing an apparatus comprising: a biopsy needle having a distal end and a proximal end, all or a portion of the biopsy needle being movable between a collapsed state and an expanded state; a sheath having a distal end and a proximal end, wherein the biopsy needle in the collapsed state is contained within the sheath, and in the expanded state at least the distal end of the biopsy needle extends from the distal end of the sheath; wherein the biopsy needle is provided with two or more sleeves, which at least partially overlap in the collapsed configuration and which cylindrically expand to provide an increased radius, relative to a radius in the collapsed state, for sampling in the expanded configuration, and wherein a cross section of the distal end of the biopsy needle in the expanded state is a substantially circular cross section.

The present teachings provide an apparatus comprising: a biopsy needle having a distal end and a proximal end, all or a portion of the biopsy needle being movable between a retracted configuration and an expanded configuration; a sheath having a distal end, a proximal end, and a longitudinal axis extending therebetween; a rotating mechanism in communication with the biopsy needle and the sheath that rotates the biopsy needle about a rotational axis of the biopsy needle as the biopsy needle moves along the longitudinal axis of the sheath; and wherein the biopsy needle in the retracted configuration is partially and/or fully located within the sheath and in the expanded configuration the distal end extends axially along the longitudinal axis.

The teachings herein surprisingly solve one or more of these problems by providing a needle that is expandable to take a sample that is larger than the size (e.g., diameter) of the needle while the needle is located within the sheath and/or delivery device. The present teachings provide a device to assist in retaining the sample within the needle once a sample is taken without the application of vacuum or with a reduced application of suction. The present teachings provide a device that resists the sample from being pulled from the needle when the needle is retracted. The present teachings provide a device that assists in cutting an attached portion of a sample or prevents removal of a sample due to an attached portion. The present teachings provide a device that rotationally cuts a sample while the needle is extended axially into a sample site.

DETAILED DESCRIPTION

The explanations and illustrations presented herein are intended to acquaint others skilled in the art with the invention, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The device of the teachings herein may be inserted into or through a larger device. The larger device may function to perform multiple different objectives during a procedure, one of which may be to take a biopsy sample, or gather a tissue sample. The device may be an endoscope, a bronchoscope, or both. The device may be a carrier for the biopsy device and needle. Preferably, the device may include a camera or some other device for providing an image. The device may include one or more channels that extend therethrough for accessing a feature at a distal end of the device. The channels may extend from a proximal end or proximal end region to a distal end or distal end region of the device. The channels may receive one or more parts of a biopsy device and direct the parts to a location of interest. Preferably, the device may have a sheath that extends from a device towards a feature of interest. The sheath may include a stylet.

The stylet may function to hold tissue in place. The stylet may function to align the needle with a feature of interest. The stylet may extend into tissue, contact tissue, grip tissue, or a combination thereof. The stylet may have a blunt end. The stylet may have a sharp tip. The stylet may extend along an axis of the sheath, a needle, or both. The stylet may be located entirely within the sheath, the needle or both. The stylet in a stored configuration may extend beyond the needle, a sheath, or both. The stylet in a stored configuration may be wholly located within the sheath, the needle or both.

The sheath may function to guide a needle to a location of interest or a feature of interest. The sheath may function to support a needle, provide cantilever support to a portion of the needle, or both. The sheath may be hollow. The sheath may extend cantilever from the device (i.e., endoscope or bronchoscope). The sheath may have a low friction inside (e.g., a polytetrafluoroethylene coating). The sheath may allow a needle to extend within an open space, a lumen, or both of the sheath. The sheath may be made of metal, plastic, a polymer, a material that is biocompatible, includes flexibility, is rigid, or a combination thereof. The sheath may provide support to a needle so that the need takes and retains a sample. The sheath may be substantially large to house any of the needles discussed herein. The sheath may be an outer containment sheath that is the inner lumen of an endoscope or other delivery device.

The needle may function to extend into a site of interest, a feature of interest, or both and remove a sample. The needle may function to be axially extended and resist deformation when contacted by a feature, tissue, or both. The needle may extend from a sheath, a deployment device, a delivery device, or a combination thereof. The needle may be free of contact with a sheath, inclusion in a sheath, or both. The needle may be about 25 gauge or larger, about 20 gauge or larger, about 18 gauge or larger, about 16 gauge or larger, 14 gauge or larger, about 12 gauge or larger, or even about 10 gauge or larger. The needle may be about 4 gauge or smaller, about 6 gauge or smaller, or even about 8 gauge or smaller. The needle may be made of one or more pieces, two or more pieces, or even three or more pieces. The needle may have an open area, an open center, a hollow space that extends through the longitudinal axis of the needle. The inside of the needle may be free of any features and may be substantially smooth. The needle may include features and/or devices within an inside of the needle (e.g., retaining features). The needle in an expanded configuration may be cylindrical, conical, parabolic shaped, "U" shaped, or a combination thereof. The needle may be made of any material that may be moved between an expanded configuration and a compressed configuration. The needle may be made of metal. The needle may be made of an elastomeric metal. Preferably, the needle may be made of nitnol. The needle may be made of one solid piece. The needle may include one or more sleeves that together form an outer wall of a needle.

The one or more outer sleeves may function to form at least a portion of a wall of the needle in the expanded configuration and the retracted configuration. The one or more outer sleeves may function to fully and/or partially surround one or more inner sleeves. The one or more outer sleeves may be an outermost surface of a needle. An entire outer wall of the outer sleeve may form an outside of the needle. The outer sleeve may have an inner wall that has a portion that contacts the sample. The outer sleeve when in a compressed state may have a perimeter (e.g., circumference) that extends about 400 degrees or less, about 360 degrees or less, or about 300 degrees or less. The outer sleeve when in a compressed state may have a perimeter that extends about 180 degrees or more, about 235 degrees or more, or preferably about 270 degrees or more. The outer sleeve when in an expanded state may have a perimeter (e.g., circumference) that extends about 360 degrees or less, about 300 degrees or less, or about 250 degrees or less. The outer sleeve when in an expanded state may have a perimeter that extends about 60 degrees or more, about 90 degrees or more, or preferably about 180 degrees or more. The perimeter of the outer sleeve when moving from a compressed state to an expanded state or vice versa may change by about 30 degrees or more, about 45 degrees or more, about 60 degrees or more, about 90 degrees or more, or even about 180 degrees or more. The outer sleeve may include a distal tip that may be blunt, sharp, angled, chamfered, distally extend to a point, or a combination thereof. The outer sleeve may extend around one or more inner sleeves in a compressed state, an expanded state or both.

The one or more inner sleeves may function to at least partially overlap an outer sleeve and complete a perimeter when the needle is in the expanded configuration, in the compressed configuration, or both. The one or more inner sleeves may function to be entirely located within the outer sleeve. The one or more inner sleeves may be partially located within the outer sleeve. The one or more inner sleeves may be collapsed by the outer sleeve. The inner sleeve may assist in expanding the outer sleeve. The inner sleeve may overlap with the outer sleeve in the compressed configuration, the expanded configuration, or both. The inner sleeve may have an inner wall that contacts the sample. The one or more inner sleeves when in a compressed state may have a perimeter (e.g., circumference) that extends about 360 degrees or less, about 300 degrees or less, about 250 degrees or less, or about 180 degrees or less (in combination when more than one sleeve is present). The one or more inner sleeves when in a compressed state may have perimeter that extends about 45 degrees or more, about 90 degrees or more, or preferably about 135 degrees or more (in combination when more than one sleeve is present). The one or more inner sleeves when in an expanded state may have a perimeter (e.g., circumference) that extends about 300 degrees or less, about 250 degrees or less, or about 180 degrees or less. The one or more inner sleeves when in an expanded state may have perimeter that extends about 60 degrees or more, about 90 degrees or more, or preferably about 180 degrees or more. The perimeter of the outer sleeve when moving from a compressed state to an expanded state or vice versa may change by about 30 degrees or more, about 45 degrees or more, about 60 degrees or more, about 90 degrees or more, or even about 180 degrees or more. The one or more inner sleeves and the one or more outer sleeves may be combined to create a needle with a hollow center.

The one or more inner sleeves and the one or more outer sleeves may function to allow the needle to expand when the needle exits the sheath and to contract to fit within the sheath as the needle is retracted. The one or more inner sleeves and the one or more outer sleeves may function to overlap each other to form a complete sleeve. The one or more inner sleeves and the one or more outer sleeves may be substantially discrete from each other substantially along the enter length of the needle. The one or more inner sleeves and the one or more outer sleeves may be connected to a portion of the needle and preferably a distal end of a needle. The one or more inner sleeves and the one or more outer sleeves may include a first end and a second end (e.g., a first circumferential end and a second circumferential end). The first end and the second end of each of the inner sleeves and the outer sleeves may form an overlapped relationship. The first end and the second end of the inner sleeve may be located proximate to the first end and the second end of the outer sleeve respectively in an expanded configuration so that a perimeter is formed. The first end of the inner sleeve and/or the outer sleeve may overlap, fold back, curve in a circular manner, or a combination thereof to be located proximate to the second end of the inner sleeve and/or the outer sleeve respectively in a compressed state. The first end and the second end of the inner sleeve, the outer sleeve, or both may be separated by a gap in the expanded configuration, the compressed configuration, or both.

The gap in the expanded configuration may be larger than the gap in the compressed configuration. The gap may function to allow the diameter of the needle to increase and decrease. The gap between the first end and the second end of the inner sleeve and/or the outer sleeve may be about 0 degrees or more, about 5 degrees or more, about 10 degrees or more, or about 15 degrees or more in the compressed state. The gap between the first end and the second end of the inner sleeve and/or the outer sleeve may be about 90 degrees or more, about 135 degrees or more, or even about 180 degrees or more in the expanded state. The gap may increase in size as the inner sleeve and the outer sleeve expand so that an opening in the needle is formed, is expanded, or both.

The opening in the needle may be located at the distal most point of the needle (i.e., the end that contacts tissue first). The opening may function to receive a tissue sample. The opening may function to hold a tissue sample. The opening may receive a core of tissue. The core of tissue may extend in the opening from the distal end towards a proximal end (i.e., an end where the user is located). One or more cutting edges may be located proximate to the opening, at an edge of the opening, or both. The inner sleeve, the outer sleeve or both may include one or more cutting edges.

The cutting edge may function to cut tissue axially as the needle is inserted into tissue. The cutting edge may assist in coring a piece of tissue when the needle is inserted. The cutting edge may be one or more chamfered edges. The chamfered edges may extend on an inside of the needle, an outside of the needle, or both. The chamfered edges may form a point when viewed in a cross-section or a circumferential line. The chamfered edges may converge to form a point. The chamfered edges may extend from an inside or an outside of the needle to an edge to form a point in a cross-section. The chamfered edge may be located at a distal end, proximate to a distal end, proximate to an opening in the needle, or a combination thereof. The cutting edges, the chamfered edges, or both may be moved along the longitudinal axis of the sheath, the needle, or both during sampling. The cutting edges, the chamfered edges, or both may be rotated while the needle is moved axially along the longitudinal axis by one or more bias rotating mechanisms.

The one or more rotating mechanisms may function to rotate a needle, axially move a needle, or both. The rotating mechanism may rotate the needle when moving in the distal direction, the proximal direction, or both. The rotating mechanism may rotate the needle 15 degrees or more, 45 degrees or more, 90 degrees or more, 180 degrees or more, or even about 360 degrees or more during one sampling movement. The rotating mechanism may include one or more bias devices.

The one or more bias devices may function to rotate the needle, axially move the needle, or both. The one or more bias devices may move the needle through the sheath. The one or more bias devices may move the needle from the proximal end to the distal end or vice versa. The one or more bias devices may only rotationally move the needle. The one or more bias devices may be part of the needle, part of the sheath, or a discrete part. The one or more bias devices may be connected to the sheath, the needle, or both. The one or more bias devices may apply a rotational force to the needle so that the needle rotates as the needle axially moves. The one or more bias devices may be a spring. The one or more bias devices may be an elastomeric material. The one or more bias devices may store kinetic energy. The kinetic energy may apply a force in the axial direction, in a rotational direction, or both. The bias device may work in conjunction with a rotating mechanism. The bias device may be used in lieu of rifling or in addition to rifling.

The rifling may function to rotate the needle about the longitudinal axis (or rotational axis). The rifling may be grooves in a surface of the needle, the sheath, or both. The rifling may be a projection that extends from the needle into a groove of the sheath. The rifling may be a projection on the stylet that extends into a groove inside the needle or vice versa. The groove inside the needle could also serve to retain a sample in the needle. The rifling may be a projection in the sheath that extends into a groove of the needle or vice versa. The rifling of the needle may be complementary to the rifling of the sheath. The rifling may generate about 0.5 turns or more, about 1 turn or more, about 2 turns or more, about 3 turns or more, or even about 4 turns or more for the full movement of the needle during a sampling movement (i.e., from a stored position to a sampling position). The rifling may extend about an inner circumference of the sheath, an outer circumference of the needle, or both. The rifling may have one or more complementary members that extend into the rifling to assist in rotating the needle. The one or more complementary members may be one or more posts.

The one or more posts may function to rotate a needle, extend a needle along an axis, or both. The one or more posts may function to guide the needle through the sheath, the delivery device, or both. The one or more posts may extend from the sheath, the needle, or both. The one or more posts may one or more projections that extend outward and fit within the rifling. The one or more posts may be a helical projection that extends outward and fits within the rifling. The one or more posts may be located apart from each other so that the posts are retained within the rifling and prevented from being removed from the rifling. When more than one post is present the posts may be longitudinally offset. Preferably, the posts are located on the needle and the rifling is located within the sheath. The rifling may work in conjunction with a retaining mechanism or be used in lieu of a retaining mechanism.

The one or more retaining mechanisms may function to prevent a sample from being removed from a needle. The one or more retaining mechanisms may function to prevent a sample from being removed by an attached portion of the sample. The one or more retaining mechanisms may function to create one way movement of a sample. The one or more retaining mechanisms may assist in detaching a sample from a biopsy site. The retaining mechanisms may be located along an entire length of the needle. The retaining mechanisms may be located proximate to the distal end of the needle. The retaining mechanisms may replace the need for vacuum. The retaining mechanisms may be used with vacuum. The retaining mechanisms may be an integral part of the needle. The retaining mechanisms may be a separate piece that is added into the needle. The retaining mechanisms may be located at a distal end of the needle. The retaining mechanisms may be a piece that tapers as the piece extends from the distal end towards the proximate end. The retaining mechanisms may include an inlet opening and a retention opening.

The one or more inlet openings may be an opening that functions to allow a sample to pass into the needle. The one or more inlet openings may be located proximate to the distal end of the needle. The one or more inlet openings may have a diameter that is substantially the same as the needle. For example, if the needle is a 10 gauge needle then the opening is a 10.5 or 11 gauge opening. The inlet opening may have a size that is within about 2 gauge or less, about 1 gauge or less, or preferably about 0.5 gauge or less of the needle. The retaining mechanism may taper as the retaining mechanism extends from the inlet opening to the retention opening. The retaining mechanism may extend inward as the retaining mechanism extends from the distal end towards the proximal end.

The one or more retention openings may function to prevent movement of a sample in the distal direction. The one or more retention openings may function to grip tissue so that the tissue is prevented from moving in the distal direction. The retention openings may allow a tissue sample to extend through the retaining mechanism in the sampling direction and then prevent the sample from moving in the retention direction. The retention openings may be at an end of a conical retaining mechanism. The retention opening may be located towards the center of the needle relative to the inlet opening. The retention opening may be an opening on the proximal end of the retaining mechanism that is smaller than the inlet opening. The retention opening may be smaller than the inlet opening by about 1 gauge or more, 2 gauge or more, even about 2.5 gauge or more, about 4 gauge or less, or about 3 gauge or less. The retention opening may locally decrease the internal diameter of the needle. The retaining mechanism when it includes a retention opening may be flexible so that the retention opening during sampling is moved towards an inner wall of the needle. The retaining mechanism may wrap an inner wall of the needle. The retaining mechanism may extend about 90 degrees or more, about 135 degrees or more, about 180 degrees or more, about 270 degrees or more, or even about 300 degrees or more about the inner wall of the needle. The retaining mechanism may extend about 360 degrees or less about the inner wall of the needle. The retaining mechanism may be free of an inlet opening and a retention opening. The retaining mechanism may extend at an angle from the distal end towards the proximal end. The retention mechanism may be a plurality of hairs.

The plurality of hairs may function to extend from the distal end towards the proximal end. The plurality of hairs may function to increase friction on a sample relative to a needle that has a smooth inner surface. The plurality of hairs may penetrate the sample. The hairs may include barbs that grip a sample. The plurality of hairs may reduce the diameter of the needle so that removal of a sample is prevented. The plurality of hairs may made of a rigid material or a semi-rigid material that moves as the sample extends in a sampling direction and prevents movement when a sample extends in the retention direction. The hairs may be made of polyurethane, silicone, butyl, polycarbonate urethane, or a combination thereof. Preferably, the hairs are not made of metal. The hairs may be extruded in a sheet and then secured within a needle. The hairs may be attached within a needle by bonding. The hairs may be formed by clam shell molding and inserted in the needle. The hairs may be a series of rings. The hairs may extend less than 360 degrees around an inside of a needle. The hairs may be located on opposing sides of an inside of a needle (i.e., about 180 degrees apart). The plurality of hairs may be used with scales, in addition to scales, or without scales.

The scales may function to retain a sample within the needle. The scales may be made of the same material as the hairs, connected in the same manner as the hairs, or both, the teachings of which are incorporated into the teachings of scales. The scales may extend from the distal end towards the proximal end. The scales may have a sharp tip. The scales may have a blunt tip. The top of the scales may extend towards a center of a needle so that as a sample is moved from the proximal end towards the distal end, movement of the sample is restricted and/or prevented. The scales may be similar to fish scales or snake scales. The scales may include barbs that grip a sample. Rows of scales may be offset relative to each other. For example, a tip of one row may be offset to tips of an adjacent scale tip. The scales may be placed in a shingle configuration. The scales may be a series of rows and one row may overlap the subsequent row.

The overlap region may function to restrict reversion of a sample. The overlap region may function to extend a top of a scale towards the center of a needle. The overlap region may be a region where one shingle extends over and covers a part of another shingle so that the overlapping shingle extends towards a center of the needle. The overlap region may be a region where a portion of one scale extends over and covers a portion of two or more adjacent scales. The overlap region and scales may be used in conjunction with or be replaced by a door.

The door may function to cover an inlet opening of the needle. The door may function to disconnect a sample from a site of interest. The door may cut a sample. The door may trap a sample. The door may close an inlet opening of the needle. The door may include a sharp edge. The door may include a sharp tip that both assists in penetrating tissue and assists in cutting attached tissue. The door may be moved between an open position and a closed position. The door may be moved about a pin, about a hinge, or both.

The one or more pins may function to allow for rotational movement of a door. The one or more pins may function to attach a movable door to the needle. The one or more pins may prevent the door from moving axially relative to the needle. The pins may function to be an axis that the door rotates about. The one or more pins may permit movement of a door between an open position and a closed position by a rotation device.

The rotation device may function to move the door between an open position and a closed position. The rotation device may function to move the door so that the door cuts attached tissue, removes a contiguous piece of tissue, caps tissue within the needle, allows tissue to be removed despite the tissue being connected, or a combination thereof. The rotation device may allow the door to be moved between a sampling configuration and closed configuration. The rotation device may be actuated from the proximal end of the needle. The rotation device may include a button that opens and closes a door. The rotation device may include one or more actuation members that extend from the proximal end to the door to control movement of the door. The actuation members may be any member that functions to move the door between an open position and a closed position. The actuation members may be a strap, a wire, a cord, a rod, or a combination thereof.

The one or more control wires may function to move the door between an open position and a closed position. The one or more control wires may function to pull the door closed, push the door closed, or both. The one or more control wires may be sufficiently strong so that the door may be used to cut tissue. The one or more control wires may be sufficiently strong to move the door into a locked position. The one or more control wires may be maintained in tension to act as a lock. The one or more control wires may be used with a retention sleeve or may be replaced by a retention sleeve.

The one or more retention sleeves may function to maintain tissue within the needle after a sample has been taken. The one or more retention sleeves may function to cover an opening in the needle so that tissue is prevented from being removed from the needle. The one or more retention sleeves may be elastomeric or include an elastomeric material. The one or more retention sleeves may be made of an elastically deformable plastic. The one or more retention sleeves may be deformable. The one or more retention sleeves may have a compressed configuration and an expanded configuration.

The compressed configuration may maintain a sample within the needle. The expanded configuration may be configured so that a sample may be taken. The one or more retention sleeves may be axially movable along the needle so that the needle is closed off after a sample is taken. The one or more retention sleeves may expand when the needle is in a sampling configuration. The one or more retention sleeves may contract when the needle is in a retraction confirmation. The retention sleeves may include a distal end that is deformable. The distal end may expand to receive the needle and contract to cover a distal end of the needle. The distal end may contract to be smaller than the opening in the needle. The distal end of the retention sleeve may be the only part of the retention sleeve that is expandable and contractible. The distal end may be a bottle neck. The retention sleeve may be bottle shaped (i.e., with a small neck and a larger body). The retention sleeve may be used with vacuum, in lieu of vacuum, without vacuum, or a combination thereof. The retention sleeve may be located behind the distal end of the needle when the needle is moved in the sampling direction.

The sampling direction may be a direction where the needle is extended out from a sheath, into tissue, or both. The sampling direction may be movement of the needle towards a site of interest, into a site of interest, or both. The sampling direction may be an opposite direction as a retention direction.

The retention direction may be a direction where a sample is removed from a site of interest. The retention direction may be in a direction opposite radial expansion of a retaining mechanism. The retention direction may be a direction that prevents a sample from being removed from a needle.

The needle may have a sampling configuration where the needle is prepared to receive a sample. The needle may have a sampling configuration where the needle is open, expanded, free of doors, free of obstructions, or a combination thereof. The needle may have a sampling configuration where tissue enters the needle. The needle in a sampling configuration may have an expanded cross-section relative to the sheath. The sampling configuration may be constrained relative to an ejecting configuration.

The ejecting configuration may function to permit a sample to be removed in the retention direction. The ejecting configuration may disengage the retaining mechanisms. The ejecting configuration may allow a sample to be removed without damaging the sample. The ejecting configuration may expand the needle beyond the sampling configuration so that the needle has an expanded cross-section when compared to the sampling configuration.

The compressed configuration may function to permit the needle to be moved in and out of the sheath. The compressed configuration may function to have an inner sleeve and an outer sleeve wrap about each other so that the inner sleeve and the outer sleeve extend into a sheath. The compressed configuration may make the needle compact in a stored state. The compressed configuration may have a smaller cross-section than an expanded configuration.

The expanded configuration may function to open an inner sleeve and an outer sleeve so that a larger tissue sample may be taken (compared to a standard needle without an expanded configuration). The expanded configuration may increase a cross-sectional area as the needle extends out of a sheath. The expanded configuration may be where the needle elastically deforms and opens up.

The extended configuration may function to extend out of the sheath, into tissue or both. The extended configuration may be where the needle is extended out of the sheath and no longer is rotating about an axis.

Figures 1A, 1B, 1C:
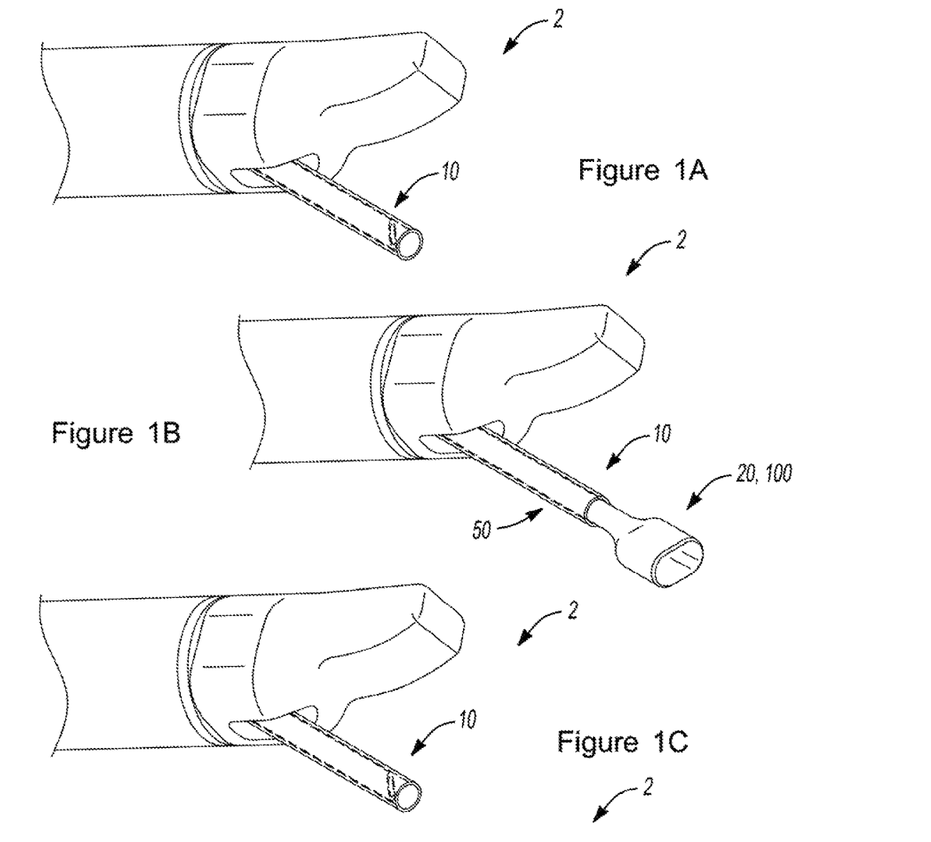
FIG. 1A illustrates a bronchoscope with a sheath extending therefrom towards a sampling location.
FIG. 1B illustrates a needle in a sampling configuration extending from the sheath.
FIG. 1C illustrates the needle retracted back into the sheath.

FIGS. 1A through 1D illustrate a sequence of collecting a tissue sample and expelling the tissue sample for testing the tissue sample. FIG. 1A illustrates a bronchoscope 2 located at a site of interest. A sheath 10 is extended from the bronchoscope 2 in preparation to collect a sample.

FIG. 1B illustrates a needle 20 extending from the distal end 50 of the sheath 10 and the bronchoscope 2. The needle 20 expands as the needle extends out of the sheath 10 into a sampling configuration 102 where the diameter of the needle 20 is larger than the diameter of the sheath 10.

FIG. 1C illustrates the needle 20 retracted back into the sheath 10 and the bronchoscope 2 after a sample is collected. The needle (not shown) is fully collapsible so that the needle fits within the sheath 10 while the needle includes a sample.

Figure 1D:
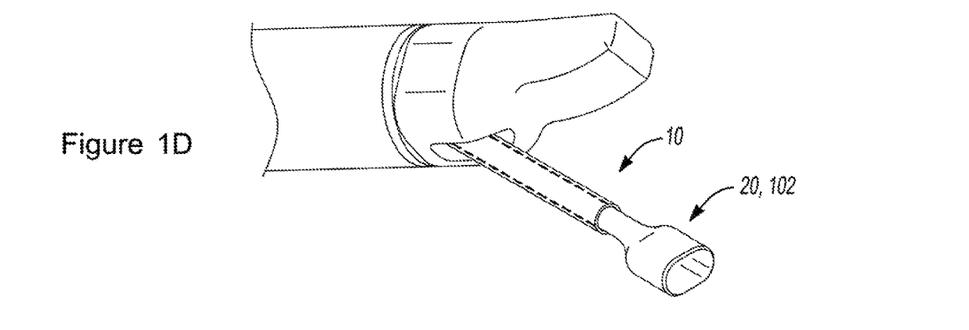
FIG. 1D illustrates the needle in an ejecting configuration so that the sample can be removed from the needle.

FIG. 1D illustrates the needle 20 extending out of the sheath 10 and the bronchoscope 2. The needle 20 is extended into an ejection configuration 102 where the needle is extended out of the sheath 10 beyond where the needle is extended in the sampling configuration 100 shown in FIG. 1B so that contact between the needle and the sample is reduced and the sample is easily removed from the needle 20.

Figure 2:
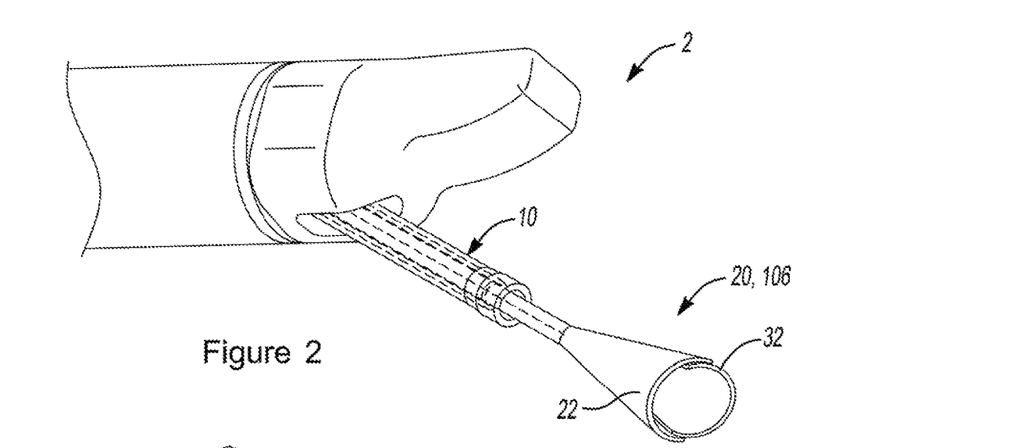
FIG. 2 illustrates a needle with a conical configuration.

FIG. 2 illustrates a bronchoscope 2 with a sheath 10 extending out of the bronchoscope 2. A needle 20 is partially extended out of the sheath 10 and is in an expanded configuration 106 where the needle is conical in shape. The needle 20 includes an outer sleeve 22 with an inner sleeve 32 located therein that is partially covered by the outer sleeve 22.

Figure 3A:
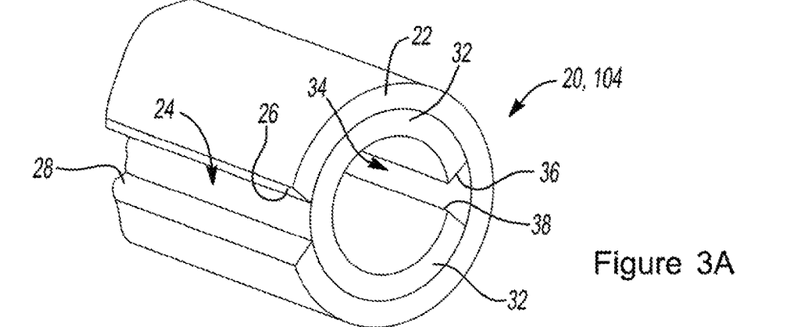
FIG. 3A illustrates a needle in a compressed configuration.

FIG. 3A illustrates a needle 20 in a collapsed configuration 104. In the collapsed configuration 104 the two sleeves of the needle 20 are compacted together to fit within the sheath (not shown). The needle 10 as shown includes an outer sleeve 22 that in the collapsed configuration 104 creates a majority of a circle (e.g., 80 percent or more) with a gap 24 located between the first end 26 and the second end 28 (however no gap may be present and the first end may overlap the second end). The outer sleeve 22 extends about an outer portion of an inner sleeve 32 so that at least a portion of the inner sleeve 32 is covered by the outer sleeve 22. The inner sleeve 32 in the collapsed configuration 104 creates a tighter circle (e.g., 85 percent or more) than that of the outer sleeve 22. The circle of the inner sleeve 32 includes a gap 34 between the first ends 36 and the second ends 38 (however no gap may be present and the first end may overlap the second end).

Figure 3B:
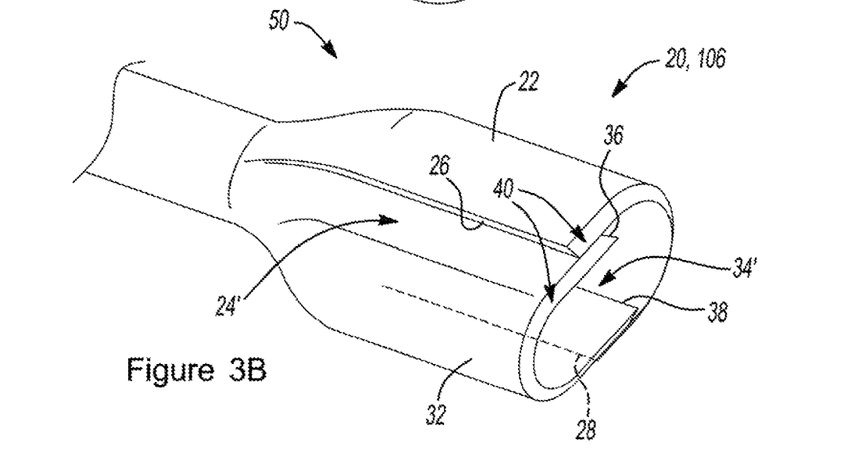
FIG. 3B illustrates a needle in an expanded configuration.

FIG. 3B illustrates a needle 20 with the distal end 50 in the expanded configuration 106. In the expanded configuration 106 the two sleeves of the needle 20 are expanded so that a diameter is created that is larger than the diameter in the compressed state (see e.g., FIG. 3A). As shown, the outer sleeve 22 is expanded so that a large gap 24' (compared to the gap 24 in the compressed state) is created between the first end 26 and the second end 28 and the outer sleeve 22 is generally "U" shaped. The inner sleeve 32 is expanded so that a larger gap 34' (compared to the gap 34 in the compressed state) is created between the first end 36 and the second end 38. The inner sleeve 32 and the outer sleeve 22 both include chamfered edges 40.

Figure 4:
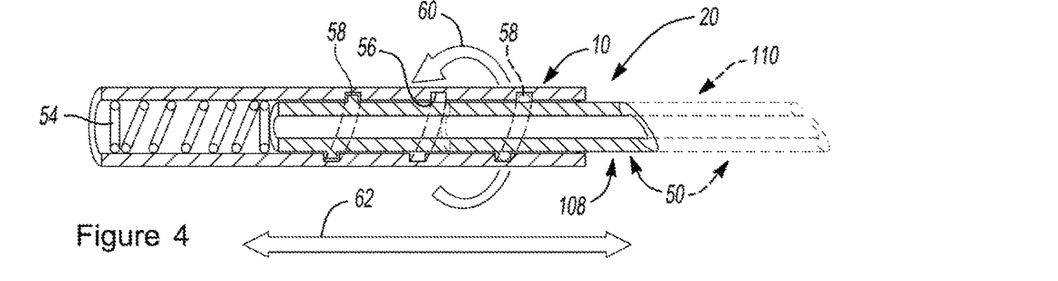
FIG. 4 illustrates a bias device that rotates the needle as the needle moves axially.

FIG. 4 illustrates a plan view of one example of needle 20. As shown, the distal end 50 of the needle 20 is shown in the extended configuration 110 and the retracted configuration 108. The needle 20 extends through a sheath 10 as the needle 20 is axially moved in the direction 62. The needle 20 as it is moved in the direction 62 is rotated in the direction 60 by one or more rotating mechanisms 58. As shown, a rotating mechanism 58 configured as rifling 56 is located on the outside of the needle 20 and/or the inside of the sheath 10 so that the needle is rotated in the direction 60 as the needle 20 moves axially in the direction 62. As illustrated, a second rotating mechanism 58 is shown that is a bias device 54 (which as shown is a spring), which is connected to the sheath 10 and the needle 20 and as the bias device 54 axially moves the needle 20, the bias device rotationally moves the needle in the direction 60.

Figure 5:
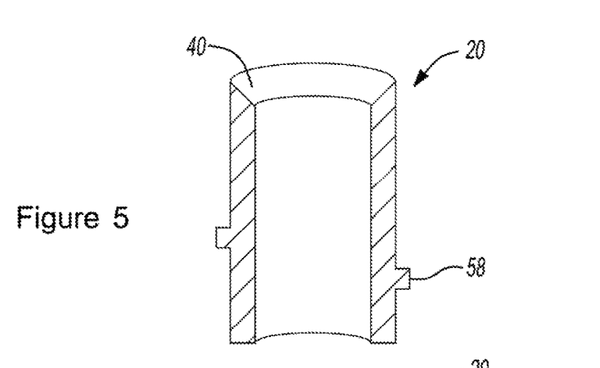
FIG. 5 is a partial cross-section of a distal end of a needle.

FIG. 5 illustrates a cross-sectional view of a needle 20. The needle 20 includes a chamfered edge 40 that chamfers from the inside out, or outside in. A rotating mechanism 58 is located on an outside of the needle 20 for rotating the needle 20 during sampling.

Figure 6A:
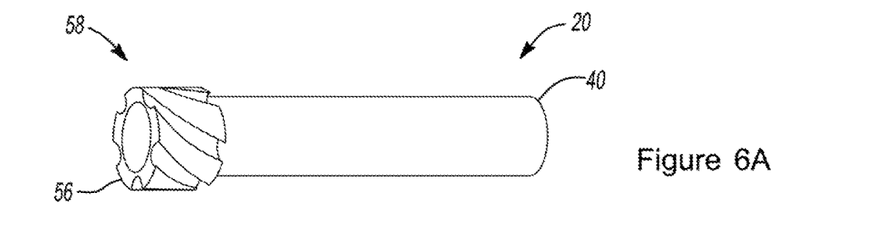
FIG. 6A illustrates a needle including a rotating mechanism.

FIG. 6A illustrates an elevation view of a needle 20. The needle 20 includes a chamfered edge 40 that chamfers from the inside out. The needle 20 includes a rotating mechanism 58 that is located towards a proximal end of the needle 20. The bias device 54 as shown is rifling 56 that rotates the needle 20 during advancement and/or retraction.

Figure 6B:
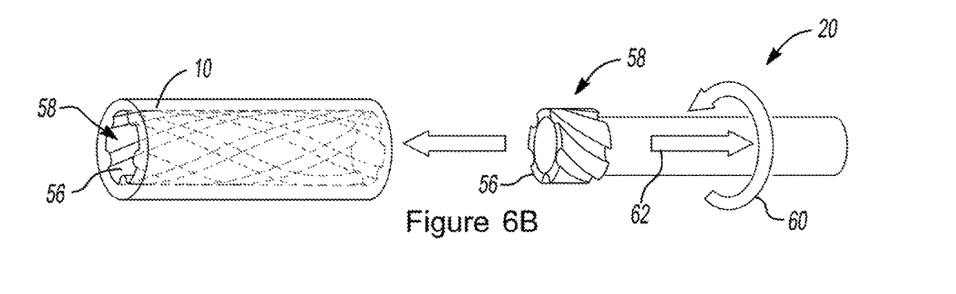
FIG. 6B illustrates an exploded view of a needle and a sheath which include complementary rotating mechanisms.

FIG. 6B illustrates an exploded view of a needle 20 extending out of a sheath 10. The sheath 10 includes a rotating mechanism 58 that as shown is rifling 56 that rotationally extends through the internal section of sheath 10. The rifling 56 extends rotationally along the longitudinal axis of the sheath 10 so that the needle 20 rotates as the needle 20 extends along the longitudinal axis of the sheath 10. The needle 20 includes a rotating mechanism 58 that includes rifling 56 that is complementary to the rifling 56 in the sheath 10. The complementary rifling 56 of the needle 20 and the sheath 10 rotates the needle 20 in the rotational direction 60 as the needle extends axially in the direction 62, along the longitudinal axis of both the needle 20 and the sheath 10

Figure 7A:
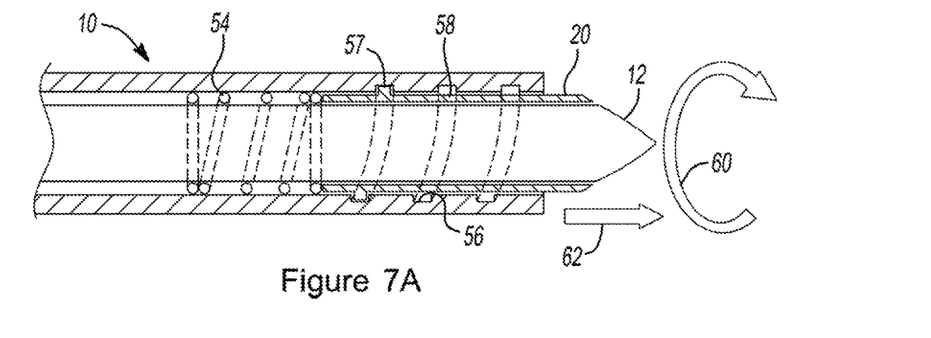
FIG. 7A illustrates a cross-sectional view of needle in a partial extended configuration.

FIG. 7A illustrates a needle 20 and a stylet 12 located within a sheath 10 and the needle 20. The sheath 10 and needle 20 include a rotating mechanism 58 so that as the needle 20 advances in the direction 62 the needle 20 is rotated in the direction 60. The needle 20 includes a post 57 that fits within the rifling 56 of the sheath 10 and as the needle 20 extends in the direction 62 the posts 57 move within the rifling 56 so that the needle 20 rotates. A bias mechanism 54 is located behind the needle 20 and assists in advancing the needle 20 in the direction 62.

Figure 7B:
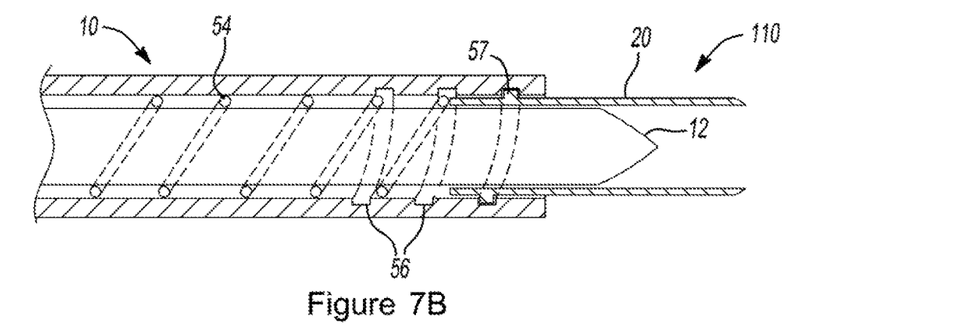
FIG. 7B illustrates a cross-sectional view of a needle in a extended configuration.

FIG. 7B illustrates the needle 20 advanced out of the sheath 10 and in an extended configuration 110. The needle 20 includes a stylet 12 and the needle 20 is advanced beyond the stylet 12. The sheath 10 includes rifling 56 that is in contact with posts 57 on the needle 20 so that the posts 57 and rifling 56 rotate the needle 20 as the needle advances. As illustrated, the bias device 54 is expanded so that the needle 20 is advanced.

Figure 8A:
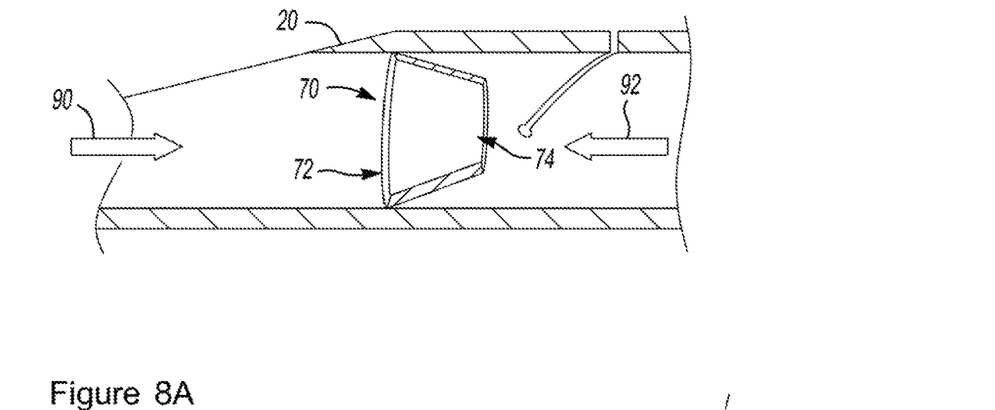
FIG. 8A illustrates a cross-sectional view of a needle and retaining mechanism.

FIG. 8A illustrates a partial cross-sectional view of a needle 20 including a retaining mechanism 70. The retaining mechanism 70 is located proximate to the mouth of the needle 20 so that a large sample can be taken and retained. The retaining mechanism 70 includes an inlet opening 72 that allows the sample to enter the needle 20 in the direction 90 and a retention opening 74 (which is smaller than the inlet opening 72) that prevents the sample from being retracted from the needle 20 in the direction 92. The retaining mechanism 70 as shown is a partial cylinder that extends partially or fully around an inside of the needle 20. The retaining mechanism 70 is connected to the needle 20 proximate to the inlet opening 72 so that the inlet opening 72 is substantially flush with the internal wall of the needle 20.

The retention opening 74 is located a distance from the internal wall. The retention opening 74 has some flexibility so that when a sample is being moved in the direction 90 the retaining mechanism 70 flexes and then if the sample is moved in the direction 92 the retention opening 74 is moved away from the internal wall to prevent movement of the sample in the direction 92.

Figure 8B:
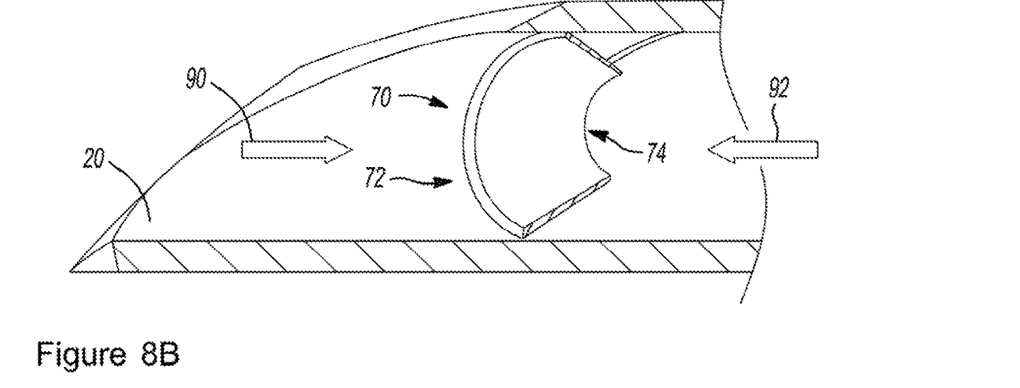
FIG. 8B illustrates a perspective view of a needle and a retaining mechanism.

FIG. 8B illustrates a perspective cross-sectional view down the needle 20. The needle 20 includes a retaining mechanism 70 that extends at least partially around the internal wall of the needle 20. The retaining mechanism 70 includes an inlet opening 72 and a retention opening 74. The inlet opening 72 is larger than the retention opening 74 so that tissue is allowed to move in the direction 90 and is prevented from moving in the direction 92.

Figure 9:
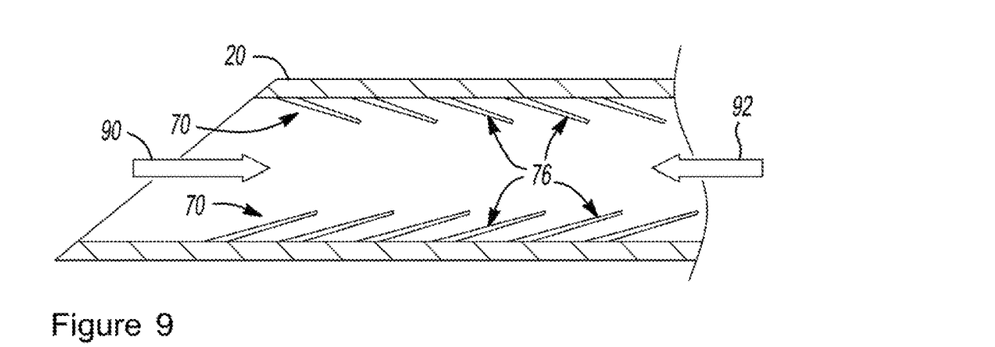
FIG. 9 illustrates a cross-sectional view of a needle and a retaining mechanism.

FIG. 9 illustrates a cross-sectional view of a needle 20 including one or more retaining mechanisms 70. As shown, the retaining mechanisms 70 are located on opposing internal walls and are configured as hairs that extend at an angle in the sampling direction 90 so that a sample can be introduced into the needle 20. The hairs 76 prevent the sample from moving in the direction 92 by creating friction against the sample so that the sample is retained within the needle 20.

Figures 10, 10A:
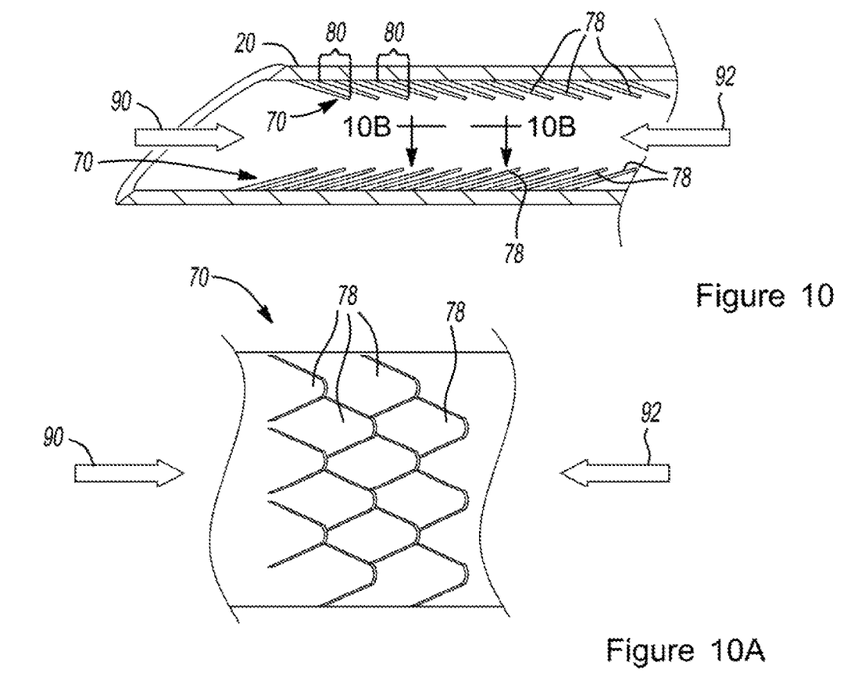
FIG. 10 illustrates a cross-sectional view of a needle including a retaining mechanism.
FIG. 10A illustrates a close-up plan view of a retaining mechanism.

FIG. 10 illustrates a cross-sectional view of a needle 20 that includes a plurality of retaining mechanisms 70. The retaining mechanisms 70 extends along the walls of the needle 20 and are angled in the direction 90. A first retaining mechanism 70 partially overlaps a subsequent retaining mechanism 70 so that an overlap region 80 is created. The retaining mechanisms 70 are configured as scales 78 that prevent movement of a tissue sample in the direction 92.

FIG. 10A illustrates an internal wall including a retaining mechanism 70 that is configured as scales 78. The scales 78 point in the direction 90 so that a low friction surface is formed during sampling of a tissue, but when the sample is moved in the direction 92 (i.e., in a direction opposite the scales) the scales 78 create friction and prevent the sample from being removed. The scales 78 as shown create an overlapping configuration so that the scales extend away (or create a raised surface) from the internal wall to prevent retraction of a sample.

Figure 10B:
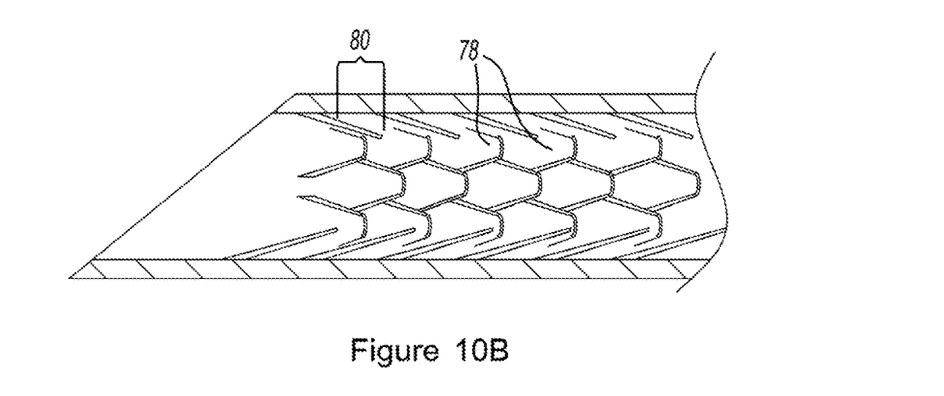
FIG. 10B illustrates a close-up plan view of the retaining mechanism of FIG. 9.

FIG. 10B illustrates a top view of the scales 78 of FIG. 9. The scales 78 have an overlap region 80 where each of the scales overlap each other.

Figures 11A, 11B:
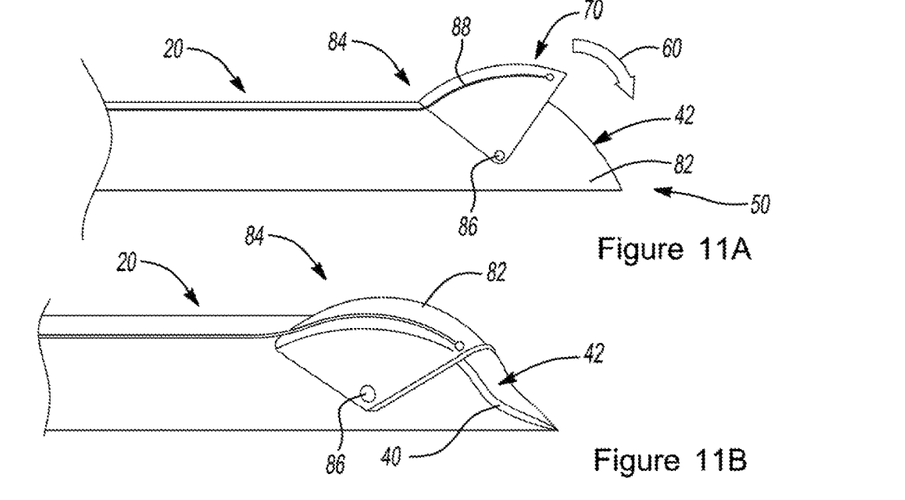
FIG. 11A illustrates a side view of a needle with a retaining mechanism at a distal end.
FIG. 11B illustrates a perspective view of a needle with a retaining mechanism at a distal end.

FIG. 11A illustrates a needle 20 with a retaining mechanism 70 located at the distal end 50. The retaining mechanism 70 includes a door 82 and a rotation device 84 that closes, by rotating in the direction 60, after a sample is taken so that the sample is retained within the needle 20. The rotation device 84, as shown, rotates about a pin 86 and may be controlled at a proximal end of the needle through the use of a control wire 88 or control button. The sample (not shown) extends through the opening 42 and into the needle 20 and is trapped in the needle within door 82 through the rotating and closing of rotation device 84 over the end of the needle 20.

FIG. 11B illustrates a perspective view of the needle 20 with the opening 42. The opening 42 includes a chamfered edge 40 that is part of the door 82. Rotation device 84 can open to collect a sample and close to maintain a sample within opening 42.

Figure 12A:
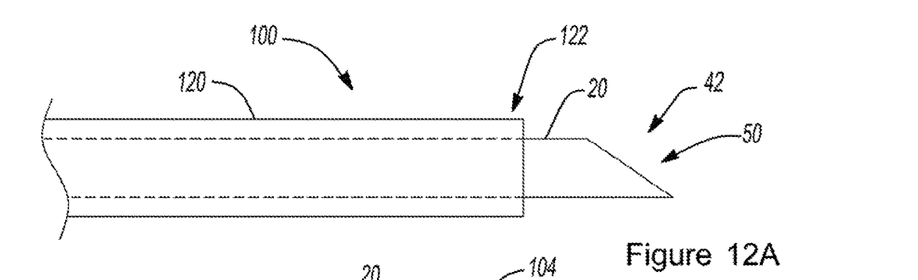
FIG. 12A illustrates a side view of a retention sleeve in the sampling configuration.

FIG. 12A illustrates a retention sleeve 120 around a needle 20. A distal end 122 of the retention sleeve 120 is in a sampling configuration 100 and is located behind the opening 42 of the distal end 50 of the needle 20 so that the needle 20 can be used to gather a sample.

Figure 12B:
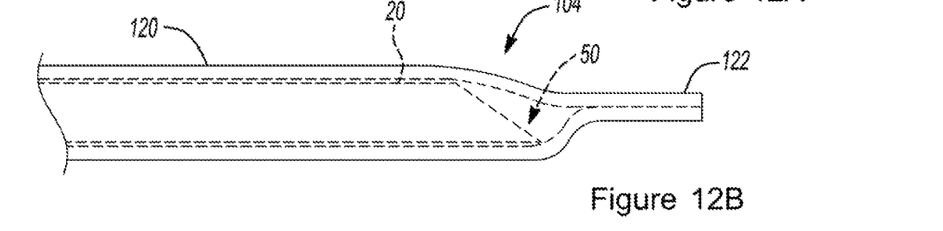
FIG. 12B illustrates a side view of a retention sleeve after a sample has been taken.

FIG. 12B illustrates the retention sleeve 120 after a sample has been taken. The retention sleeve 120 moves forward so that the distal end 122 extends over the distal end 50 of the needle 20. Once the retention sleeve 120 is beyond the distal end 50 of the needle 20 the distal end 122 of the retention sleeve moves into a compressed configuration 104 so that the sample is retained within the needle 20.

Figure 13:
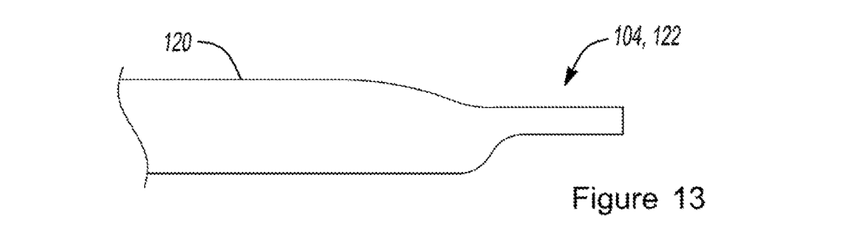
FIG. 13 illustrates a side view of a retention sleeve.

FIG. 13 illustrates the retention sleeve 122 with the distal end 122 in the compressed configuration 104.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Bronchoscope
10 Sheath
20 Needle
22 Outer Sleeve
24 Gap
26 First End
28 Second End
32 Inner Sleeve
34 Gap
36 First End
38 Second End
40 Chamfered Edges
42 Opening
50 Distal End
52 Proximal End
54 Bias Device
56 Rifling
58 Rotating Mechanism
60 Direction of Rotation
62 Direction of Movement
70 Retaining Mechanism
72 Inlet Opening
74 Retention Opening
76 Hairs
78 Scales
80 Overlap region
82 Door
84 Rotation Device
90 Sampling Direction
92 Retention Direction
100 Sampling Configuration
102 Ejecting Configuration
104 Compressed Configuration
106 Expanded Configuration
108 Retracted Configuration
110 Extended Configuration
120 Retention Sleeve
122 Distal end

We claim:

1. An apparatus comprising:
a biopsy needle having a distal end and a proximal end, all or a portion of the biopsy needle being movable between a collapsed state and an expanded state;
a sheath having a distal end and a proximal end,
wherein the biopsy needle in the collapsed state is contained within the sheath, and in the expanded state at least the distal end of the biopsy needle extends from the distal end of the sheath;
wherein the biopsy needle is provided with two or more sleeves, which at least partially overlap in the collapsed state and which cylindrically expand to provide an increased radius, relative to a radius in the collapsed state, for sampling in the expanded state;
wherein a cross section of the distal end of the biopsy needle in the expanded state is a substantially circular cross section; and
wherein an entire length of the needle is the two or more sleeves.

2. The apparatus of claim 1, wherein a distal most edge of the needle is a chamfered edge.

3. The apparatus of claim 2, wherein the two or more sleeves are the distal end of the needle.

4. The apparatus of claim 1, wherein the two or more sleeves are the distal end of the needle.

5. The apparatus of claim 4, wherein the two or more sleeves are connected to a shaft of the needle.

6. The apparatus of claim 1, wherein the two or more sleeves are generally cone shaped when in the expanded state.

7. The apparatus of claim 1, wherein a sample core which is collected becomes elongated when the biopsy needle is returned to a collapsed state within the sheath.

8. The apparatus of claim 7, wherein the two or more sleeves are generally cone shaped when in the expanded state.

9. The apparatus of claim 1, wherein an inside surface of the two or more sleeves is provided with retaining mechanisms which extend toward a center of the biopsy needle.

10. The apparatus of claim 1, wherein an inside surface of the two or more sleeves is provided with retaining mechanisms which extend toward the proximal end of the biopsy needle.

11. The apparatus of claim 1, wherein a rotating mechanism rotates about the rotational axis as the biopsy needle extends from the proximal end towards the distal end and from the distal end towards the proximal end.

12. An apparatus comprising:
a biopsy needle having a distal end and a proximal end, all or a portion of the biopsy needle being movable between a collapsed state and an expanded state;
a sheath having a distal end and a proximal end,
wherein the biopsy needle in the collapsed state is contained within the sheath, and in the expanded state at least the distal end of the biopsy needle extends from the distal end of the sheath;
wherein the biopsy needle is provided with two or more sleeves, which at least partially overlap in the collapsed state and which cylindrically expand to provide an increased radius, relative to a radius in the collapsed state, for sampling in the expanded state,
wherein a cross section of the distal end of the biopsy needle in the expanded state is a substantially circular cross section; and
wherein the two or more sleeves are connected to a shaft of the needle, and an entire length of the needle is the two or more sleeves.

13. The apparatus of claim 12, wherein a distal most edge of the needle is a chamfered edge.

14. The apparatus of claim 13, wherein the two or more sleeves are made of nitinol.

15. The apparatus of claim 12, wherein the two or more sleeves are generally cone shaped when in the expanded state.

16. The apparatus of claim 12, wherein a sample core which is collected becomes elongated when the biopsy needle is returned to a collapsed state within the sheath; an inside surface of the two or more sleeves are provided with retaining mechanisms which extend toward the center of the biopsy needle; and a rotating mechanism in communication with the biopsy needle and the sheath that rotates the biopsy needle about a rotational axis of the biopsy needle as the biopsy needle moves along a longitudinal axis of the sheath.

17. An apparatus comprising:
a biopsy needle having a distal end and a proximal end, all or a portion of the biopsy needle being movable between a collapsed state and an expanded state;
a sheath having a distal end and a proximal end,
wherein the biopsy needle in the collapsed state is contained within the sheath, and in the expanded state at least the distal end of the biopsy needle extends from the distal end of the sheath;

wherein the biopsy needle is provided with two or more sleeves, which at least partially overlap in the collapsed state and which cylindrically expand to provide an increased radius, relative to a radius in the collapsed state, for sampling in the expanded state, wherein a cross section of the distal end of the biopsy needle in the expanded state is a substantially circular cross section; and wherein the two or more sleeves are made of nitinol and an entire length of the needle is the two or more sleeves.

18. The apparatus of claim 17, wherein a distal most edge of the needle is a chamfered edge.

19. The apparatus of claim 18, wherein the two or more sleeves are generally cone shaped when in the expanded state.

20. The apparatus of claim 17, wherein a sample core which is collected becomes elongated when the biopsy needle is returned to a collapsed state within the sheath; an inside surface of the two or more sleeves are provided with retaining mechanisms which extend toward the center of the biopsy needle; and a rotating mechanism in communication with the biopsy needle and the sheath that rotates the biopsy needle about a rotational axis of the biopsy needle as the biopsy needle moves along a longitudinal axis of the sheath.

* * * * *